United States Patent
Cooper et al.

(10) Patent No.: US 6,309,631 B1
(45) Date of Patent: Oct. 30, 2001

(54) BARRIER CREAM

(75) Inventors: Graham J Cooper; Paul M Dearden, both of Salisbury (GB)

(73) Assignee: Secretary of State for Defence in Her Britannic Majesty's Government of the United Kingdom of Great Britain and Northern Ireland, Farnborough (GB)

(*) Notice: Subject to any disclaimer, the term of this patent is extended or adjusted under 35 U.S.C. 154(b) by 0 days.

(21) Appl. No.: 09/620,132

(22) Filed: Jul. 20, 2000

(30) Foreign Application Priority Data

Jul. 22, 1999 (GB) .................................................. 9917103

(51) Int. Cl.[7] ............................ A61K 7/06; A61K 31/74; A61K 7/00; A61K 7/42

(52) U.S. Cl. .................. 424/78.06; 424/70.1; 424/78.02; 424/401; 424/59

(58) Field of Search ............................... 424/78.02, 70.1, 424/59, 401, 78.06

(56) References Cited

U.S. PATENT DOCUMENTS

| | | | |
|---|---|---|---|
| 4,820,508 | * | 4/1989 | Wortzman .............................. 424/59 |
| 5,427,771 | * | 6/1995 | Grollier et al. ......................... 424/59 |
| 5,486,353 | * | 1/1996 | Billia et al. ............................. 424/59 |
| 5,695,747 | | 12/1997 | Forestier et al. . |
| 5,811,082 | | 9/1998 | Ahlnäs et al. . |

FOREIGN PATENT DOCUMENTS

| | | |
|---|---|---|
| 2533497 a1 | 2/1977 | (DE) . |
| 2 680 466 | 2/1993 | (FR) . |
| 2206282A | 1/1989 | (GB) . |
| 2211409A | 7/1989 | (GB) . |
| 2217987A | 11/1989 | (GB) . |
| 2243781A | 11/1991 | (GB) . |
| WO 96/28136 | 9/1996 | (WO) . |
| 98/01107 A1 | 1/1998 | (WO) . |

* cited by examiner

Primary Examiner—Thurman K. Page
Assistant Examiner—Rachel M. Bennett
(74) Attorney, Agent, or Firm—Nixon & Vanderhye (57) ABSTRACT

Barrier creams are described which are useful in protecting a user from burns during exposure to heat. The creams comprise a base cream with at least one of a melt additive and a reflective additive, or ideally both a melt additive and a reflective additive. The cream preferably is waterproof and has an acceptable longevity of application.

8 Claims, 7 Drawing Sheets

Fig. 1.

- Heat Dose Gauge
- Reflected Pressure Gauge
- Heated Heat Dose Gauge

Fig. 5.

- Heat Dose Gauge - no creams applied
- Heated Heat Dose Gauge - creams applied

BARRIER CREAM

This invention relates to barrier creams. More particularly, the present invention relates to barrier creams which are useful in protecting a user from burns during exposure to heat.

Traditional barrier creams place a passive barrier between the skin and the environment which prevents the access of chemicals generally to the surface of the skin. More recently, creams have been developed which contain an active ingredient which prevents a chemical from having an effect on the skin, for example by denaturing the chemical.

Additionally, creams are known which protect the skin from the adverse effects of ultraviolet light or sunlight in order to prevent sunburn. However, at present there are no creams available which prevent or minimise the damage caused to skin by burning as a result of exposure to heat per se, particularly heat from explosive events, or to infra-red light. In particular, there are no protective or barrier creams available which prevent burns in a military or accident scenario. In military scenarios it is known that up to 10% of all casualties may suffer burns, the incidence of burns may even rise as high as 40–60%.

It has long been the case that burns are generally prevented by the use of protective clothing, and materials are available which offer a high degree of protection from flame burns. Even lightweight materials are able to provide some measure of protection against flash burns. However, areas such as the hands and face are extremely vulnerable and are often not protected by clothing. For example, the loss of manual dexterity experienced by wearing protective gloves can be quite substantial, as can the impairment of the field of vision from wearing protective headgear. For these reasons, it is often the case that workers in potentially hazardous environments who find protective gloves and headgear particularly cumbersome will not wear them when the perceived risk of danger is low, with the result that incapacitating burns may arise in the event of an incident. In such situations it is desirable to provide an alternative method of burns protection.

In this respect the present inventors have developed a barrier cream for use in mitigating at least high flux, radiated and convected heat from reaching a surface to which the cream is applied.

Accordingly, the present invention provides a barrier cream for the mitigation of burns, the cream comprising a base cream and at least one of a melt additive and a reflective additive.

The present inventors have found that such additives are effective in increasing the time taken for radiated and convected heat to reach a surface to which the cream has been applied. Where the cream is applied to skin, the potential for burn injuries, particularly from explosive effects, is reduced.

The cream of the present invention is preferably applied to the skin. However, it may also be applied to fabrics, particularly clothing, or even to instruments which are sensitive to heat. Where the cream is applied to fabric, it may be applied to one or both sides of the fabric or may be impregnated through the fabric or its fibres.

The present inventors have found that barrier creams offering reflective protection are useful in the prevention of burns, particularly where the cream is able to reflect infra-red radiation. However, the present inventors have found that a cream comprising both reflective additive(s) and melt additive(s) gives better protection to the user.

In this respect the present invention further provides a barrier cream for the prevention of burns, particularly flash burns, the cream comprising a base cream, a melt additive and a reflective additive.

Preferably, the reflective additive reflects infra-red radiation.

The base cream is preferably a pharmacologically acceptable base cream, for example a proprietary base cream such as an aqueous cream, a zinc based cream or an oil based cream, for example a glycerol based cream.

Where the surface to be protected is skin, then it is highly desirable that the melt additive is non-toxic, moreover it should be non-irritant or hypoallergenic.

Preferably, the melt additive has a latent heat of fusion of at least 50 $Jg^{-1}$. The latent heat of fusion should be as high as possible in order to provide optimum protection against thermal attack; preferably at least 150 $Jg^{-1}$ and ideally at least 200 $Jg^{-1}$. However, the choice of the melt additive is also, in part, determined by its other properties such as solubility in the base cream, viscosity and melting point.

Conveniently, the melt additive has a melting point below 55° C., preferably below 50° C. Ideally, the melting point is above 40° C.

Preferably, the melt additive comprises an alkali metal salt, alcohol, fat or wax, more preferably a fatty acid or derivative, for example, a fatty acid ester.

In a most preferred embodiment, the melt additive is selected from the group comprising methyl 4-(hydroxymethyl) benzoate, 4-phenylbutyric acid, 1-4-benzodioxan-6-carboxaldehyde, methyl 4-methoxybenzoate, 4-methylbenzhydrol and methyl 7-oxooctadecanoate, cetyl alcohol or sodium thiosulphate. Of these, methyl 7-oxooctadecanoate and cetyl alcohol are preferred because of their high latent heat of fusion (222.3 and 244.1 $Jg^{-1}$ respectively), giving them a great ability to absorb heat without becoming hot, thus rendering them useful in the prevention of burns.

The reflective additive preferably comprises a salt of a transition metal, preferably a titanium or iron salt. In preferred embodiments, the salt may be selected from the group comprising zinc and titanium oxide, zinc plus a mixture of titanium and iron (III) oxide, titanium dioxide, iron (III) oxide, titanium oxide and iron (III) oxide, magnesium silicate and carbon black. Ideally, the reflective additive is able to reflect radiation at infra red and visible wavelengths.

It is preferred that the barrier cream comprises 5–75% w/w of the at least one of the melt additive and reflective additive (i.e. the summed weight of the melt additive and reflective additive is 5–75% of the total weight of the barrier cream). It is further preferred that the cream comprises 0–25% w/w of the melt additive, most preferably 10–20%. It is preferred that the cream comprises 0–50% w/w of the reflective additive, most preferably 10–50%. However, the preferred and most preferred concentrations of both the reflective additive and melt additive depend on the nature of the cream base. In the case of a zinc cream, it is preferred that the cream comprises 5–40% w/w of the at least one of the melt additive and reflective additive. It is most preferred that a zinc cream comprises 5–20% w/w of the reflective additive and 0–20% w/w of the melt additive. In the case of an oil based cream, it is preferred that the cream comprises 35–75% w/w of the at least one of the melt additive and reflective additive. It is most preferred that an oil based cream comprises 35–55% w/w of the reflective additive and 0–20% w/w of the melt additive.

Ideally, the cream has a longevity of application, that is, is resistant to inadvertent removal by abrasion against clothing and the like and is preferably waterproof, not only to water arising from perspiration but to immersion in water.

In a preferred embodiment the cream may comprise a colouring additive according to the intended purpose of the cream. For example, for military applications one may select a brown/green colouring additive so that the cream may be used in the place of a conventional camouflage cream.

Embodiments of the invention will now be described, by way of example only, with reference to the following drawings of which.

EXAMPLE 1

Trials Using Heat Gauges
Selection of Ingredients:

The properties of the preferred ingredients are shown in the following tables. Note that the zinc cream base was "zinc and castor oil BP".

TABLE 1

| CREAM | COMPOSITION |
| --- | --- |
| A | Zinc/$TiO_2$ (5% $TiO_2$, particle size 0.2–0.3 $\mu$m) |
| B | Zinc cream and 5% oxide mixture[1] |
| C | Glycerol + 50% $TiO_2$ |
| D | Glycerol + 50% oxide mixture[1] |

[1]Oxide mixture is prepared by grinding equal weights of $TiO_2$ and $Fe_2O_3$, mixing them into a slurry with water, evaporating the water and grinding the residue into a dark red brown powder.

TABLE 2

Properties of melt additive.

| Sample | Melting point (° C.) | Onset of melting (° C.) | Latent heat of fusion ($Jg^{-1}$) |
| --- | --- | --- | --- |
| methyl 4-(hydroxymethyl) benzoate | 47–50 | 44.2 | 123.7 |
| 4-phenylbutyric acid | 50–52 | 48.5 | 131.8 |
| 1-4-benzodioxan-6- | 50–52 | 48.5 | 125.6 |

TABLE 2-continued

Properties of melt additive.

| Sample | Melting point (° C.) | Onset of melting (° C.) | Latent heat of fusion ($Jg^{-1}$) |
| --- | --- | --- | --- |
| carboxaldehyde | | | |
| methyl 4-methoxybenzoate | 49–51 | 46.6 | 113.6 |
| 4-methylbenzyhydrol | 50–54 | 51.9 | 118.2 |
| methyl 7-oxooctadecanoate | 50–52 | 46.6 | 222.3 |
| Sodium thiosulphate | 48–52 | 48.0 | 184.4 |
| Cetyl alcohol | 46–51 | 47.2 | 244.1 |

TABLE 3

Composition of cream formulations

| Cream | Base composition | Reflection additive | Melt additive |
| --- | --- | --- | --- |
| A | Zinc | 5% $TiO_2$ | Nil |
| B | Zinc | 5% $TiO_2$/$Fe_2O_3$ (1:1) | Nil |
| C | Glycerol | 50% $TiO_2$ | Nil |
| D | Glycerol | 50% $TiO_2$/$Fe_2O_3$ (1:1) | Nil |
| E | Glycerol | 45% $TiO_2$ | 10% methyl 7-oxooctadecanoate |
| F | Glycerol | 45% $TiO_2$/$Fe_2O_3$ (1:1) | 10% methyl 7-oxooctadecanoate |

A total of 20 trials were carried out with only one cream type being used on each individual trial. Four trials were carried out with each of creams A–D and two trials for each of E and F.

Four pairs of heat dose gauges were positioned around an explosive charge selected in known manner to give a high thermal output for a given charge mass.

Figure 1:
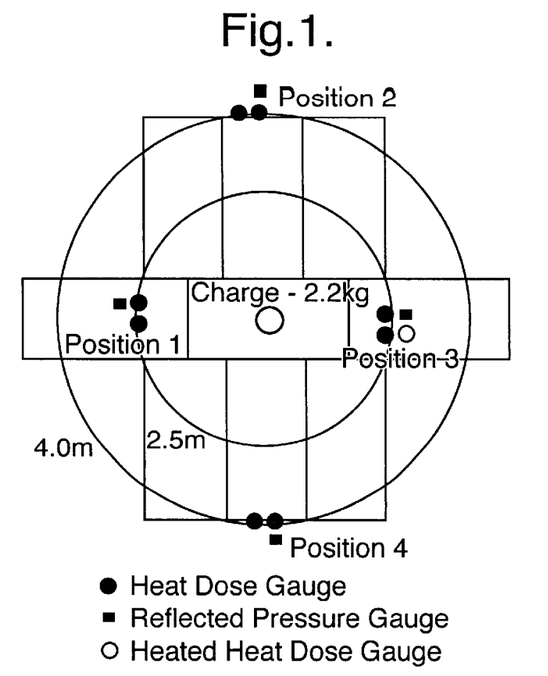
FIG. 1 shows the positioning of the instrumentation used to measure heat and resistance to heat, wherein the heat is generated by an explosive charge.

The charge was selected to give minimal fragmentation and hence minimal damage to the heat dose gauges. FIG. 1 shows the positioning of the instrumentation used to measure heat and resistance to heat in relation to the charge. Positions 1 and 3 are 2.5 m from the charge, while positions 2 and 4 are 4.0 m from the charge. The charge was approximately 2.0 m above the ground and each of the gauges was 0.25 m above the charge height. Of each pair of gauges one was covered with cream and the other was not covered with cream so as to act as a control reference and the results from each gauge were compared. The relative heat dose is the ratio of the heat dose experienced by a heat gauge covered with cream to the heat dose experienced by the associated heat gauge which is not covered with cream.

Each of the candidate creams was applied to the gauge surfaces manually, but each cream was applied in a slightly different manner to represent a realistic in situ loading. The masses of applied creams were determined for each application. An additional gauge, mounted at position 3 and shown in FIG. 1 as the heated heat dose gauge ('heated gauge'), was preset to a temperature of between 33 and 36° C. by means of an electrically controlled heating plate. This temperature corresponds to surface body temperature. The heated gauge was used creamed/uncreamed on alternate test runs. In order to assess any variances between explosions, reflected pressure gauges were mounted at each position 1–4.

Figure 2:
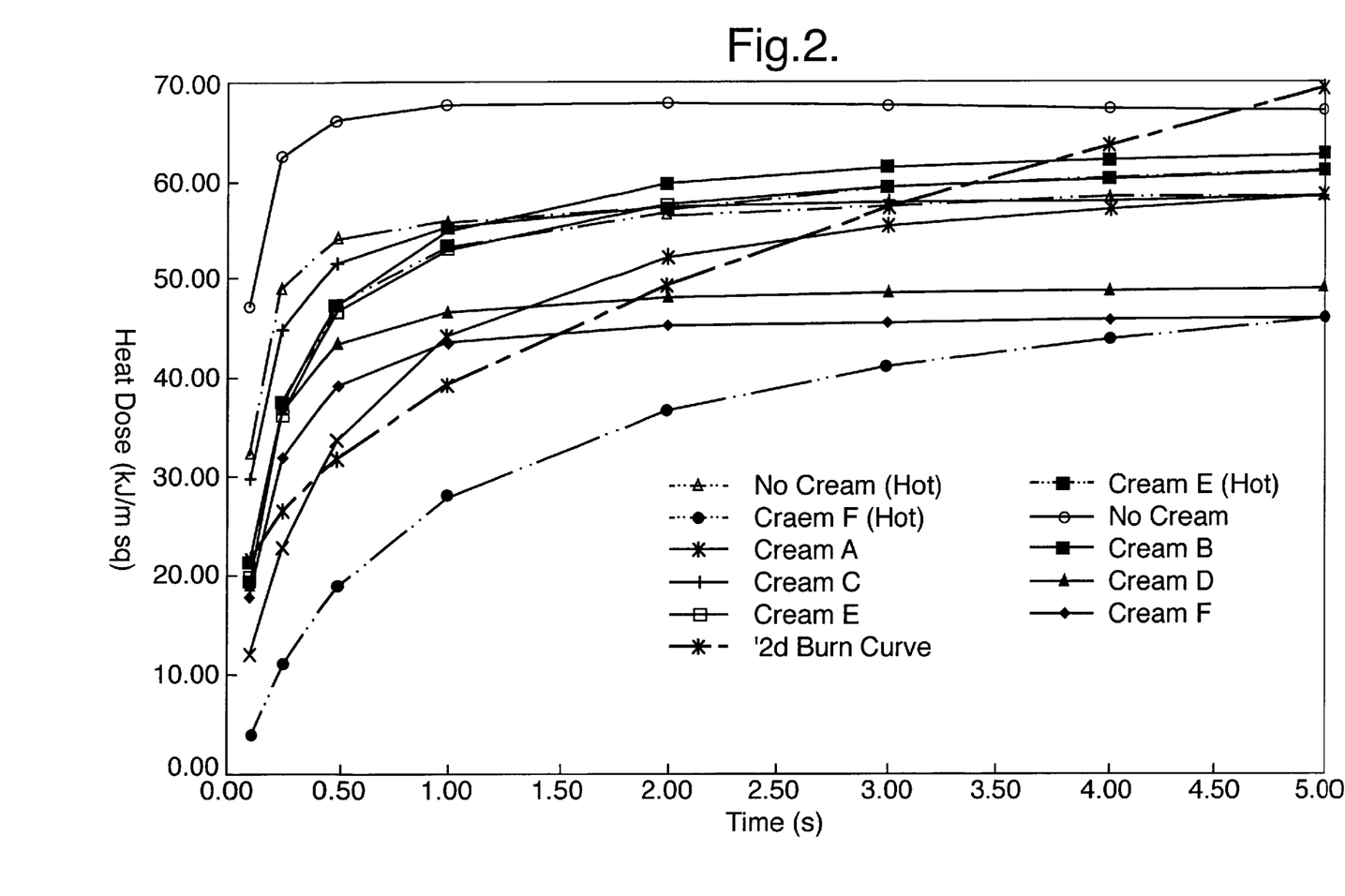
FIG. 2 is a graph showing the heat dose performance data for a number of examples A–F of the cream in accordance with the present invention as measured using the instrumental arrangement of FIG. 1.

The performance of each of the example creams A–F is shown in FIG. 2 for the heat gauges at positions 1 and 3, 2.5 m from the charge. The figure shows the mean values of heat dose measured at discrete time intervals after the explosion. A low heat dose signifies good performance of a thermal barrier cream. All creams tested show good performance within the first second after detonation, but there is some variance in the overall performance of the creams. From the data collected from the unheated gauges, cream F appears to be the most effective cream of the six tested, since it minimises heat dose in the period between 1 and 5 seconds after the explosion.

Figure 4:
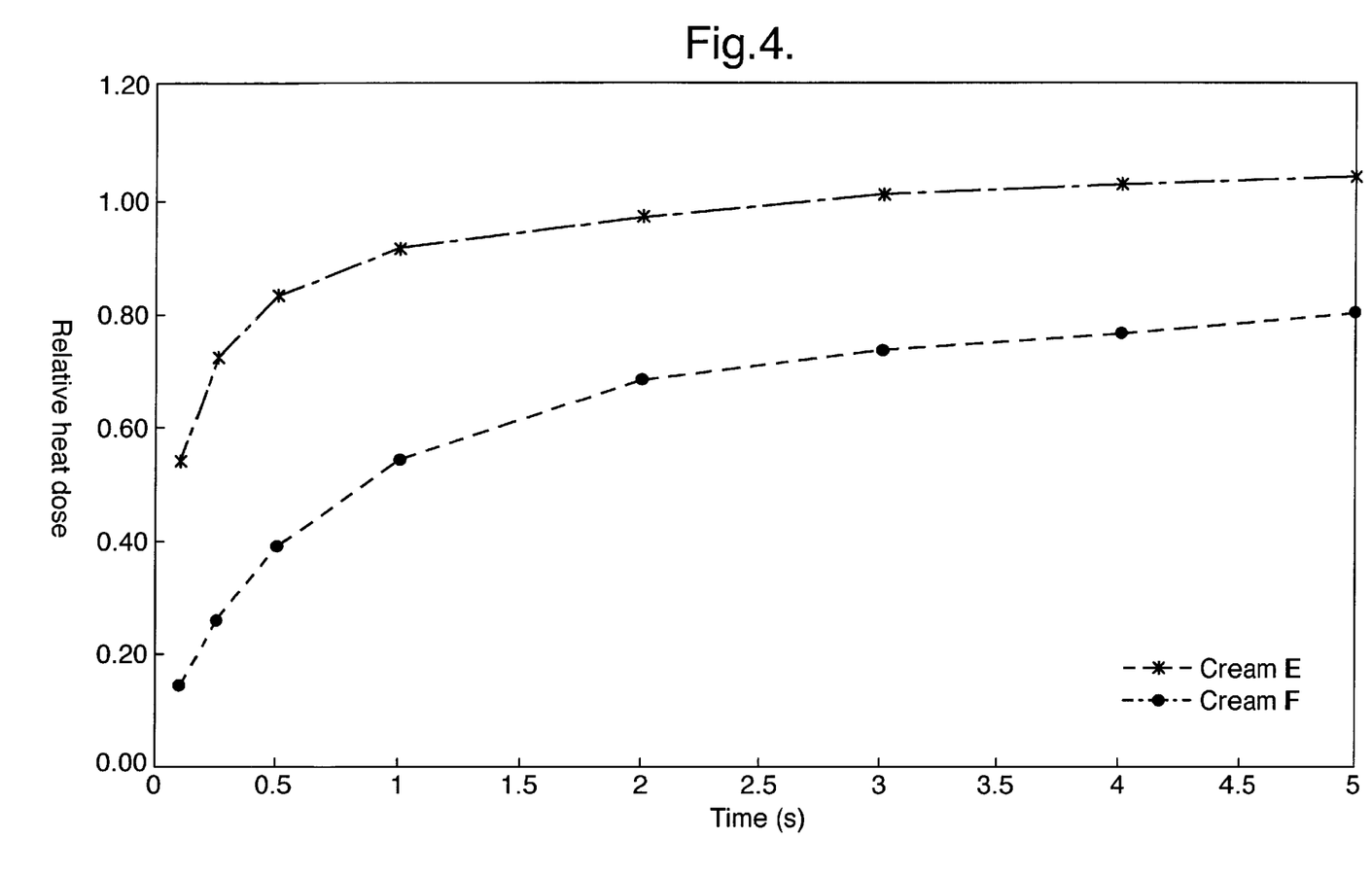
FIG. 4 shows further relative heat dose performance data for creams E and F as measured by the heated gauge using the instrumental arrangement of FIG. 1.

FIG. 2 also shows the heat dose performance data of creams E and F when the creams are heated to a temperature corresponding to surface body temperature i.e. the data obtained from the heated gauge. This can be seen more clearly in FIG. 4 which shows the relative heat dose performance data for creams E and F on the heated gauge. From FIG. 2, it can be seen that the performance of cream E is not appreciably improved by heating to a temperature corresponding to surface body temperature. However, the performance of cream F is markedly improved by such heating.

FIG. 2 also indicates the calculated heat dose required to produce a second degree burn at a distance of 2.5 m from the explosion. Creams considered to be effective in minimising $2^{nd}$ degree burns will be below the theoretical $2^{nd}$ degree burns curve. At 2.5 m, only cream F when heated to a temperature corresponding to a surface body temperature achieves this for the whole of the considered time period. The fact that some of the creams in accordance with the present invention do not appear to prevent $2^{nd}$ degree burns does not indicate that these creams do not show advantageous properties in the mitigation of burns. All of the examples A–F provide some protection against the thermal effects of the explosion. Note that the second degree burn curve is provided to highlight the differences between the creams when viewing the mean values only.

FIG. 2 also shows the effects of using a 1:1 mixture of $TiO_2$ and $Fe_2O_3$ (hereinafter 'the oxide mixture') as a reflective additive instead of $TiO_2$.

Comparisons of the data for example C with those for D, and data for E with those for F suggest that where the creams had a glycerol base, the oxide mixture gave improved performance compared with titanium oxide. However, for creams with a zinc base, it appears from FIG. 2 that titanium oxide gives better performance than the oxide mixture.

A comparison of the data for creams D and F indicates that the addition of a melt additive improves the performance of the cream. However, a comparison of the data for creams E and C indicates that the addition of a melt additive is not beneficial for the whole of the period in which the heat dose is measured. Note that whilst a small amount of melt additive was present in both creams E and F, the content of reflective additive was lower than the corresponding creams C and D (45% rather than 50%). This may explain the inconsistency between these observations.

Figure 3:
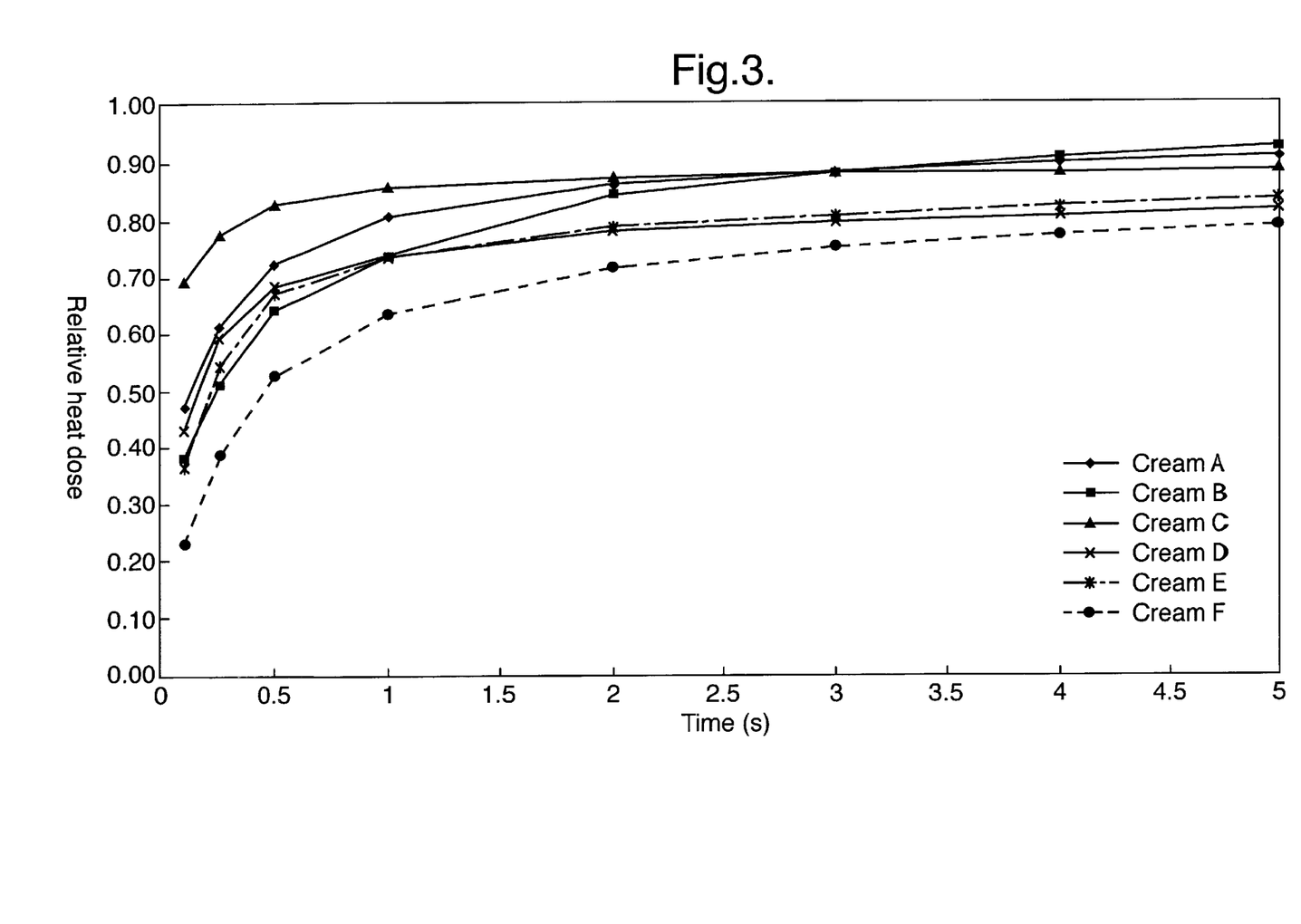
FIG. 3 shows the relative heat dose performance data for examples A–F of the cream for the gauges positioned 4 m from the explosion as measured using the instrumental arrangement of FIG. 1.

FIG. 3 shows the relative heat dose performance data for the gauges positioned 4 m from the explosion. The data shown are mean values. All creams reduced the heat dose experienced by the gauges. It can be seen that cream F is the most effective thermal barrier cream. Cream F performs better than cream E and cream D performs better than cream C, consistent with the results obtained from the probes positioned 2.5 m from the explosion. However, in contrast with the results obtained from the nearer probes, the performance of cream B at 4 m is better than that of A for the first 3 seconds after the explosion. Furthermore, a comparison of data for F with that for D and a comparison of data for E with that for C suggest that the addition of a melt additive improves cream performance as measured at 4 m from the explosion.

It is worth noting that the mean heat doses experienced by all gauges, covered and uncovered by cream, positioned 4 m from the explosion were lower than that required to produce $2^{nd}$ degree burns.

EXAMPLE 2

Figure 5:
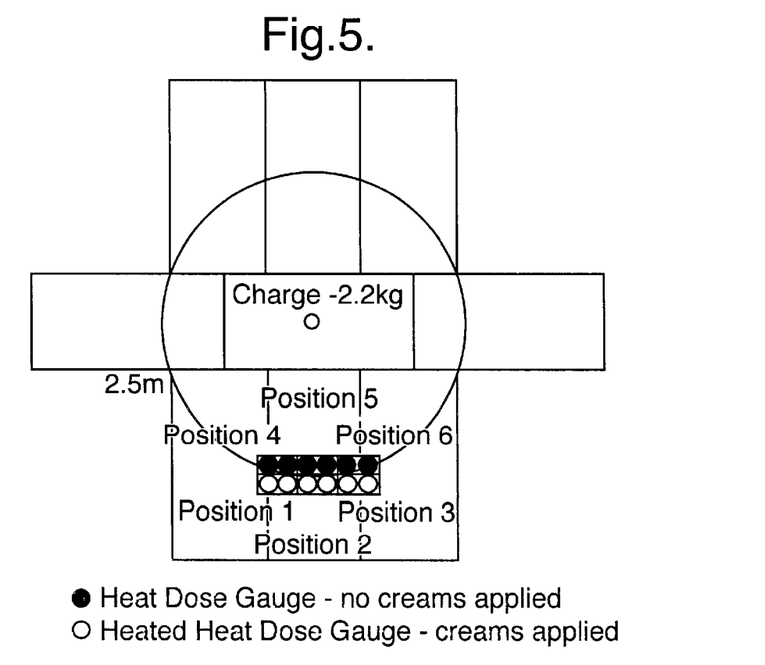
FIG. 5 shows the positioning of the instrumentation in a further experiment to measure heat and resistance to heat, wherein the heat is generated by an explosive charge.

For a second phase of testing, twelve heat dose gauges were positioned 2.5 m from an explosive charge according to the layout shown in FIG. 5. Six of the twelve gauges were fitted with an electrically controlled heating element in the base plate, each gauge having its pre-detonation temperature maintained at surface body temperature (33–36° C.). The other six control gauges used as references were not heated. The heated gauge of each pair was coated with the test cream for that trial, the results from the creamed and uncreamed gauges were then compared for each trial. Each of the creams tested used the reflective additive comprising a 1:1 mixture of $TiO_2$ and $Fe_2O_3$ (the oxide mixture) which was found to be advantageous in example 1.

The formulation of the creams tested is shown in Table 4

TABLE 4

Compositions of cream formulations

| Cream | Base cream | Reflection additive | Melt additive |
|---|---|---|---|
| G | Zinc | 10% $TiO_2/Fe_2O_3$ (1:1) | Nil |
| H | Zinc | 10% $TiO_2/Fe_2O_3$ (1:1) | 10% sodium thiosulphate |
| I | Glycerol | 50% $TiO_2/Fe_2O_3$ (1:1) | Nil |
| J | Glycerol | 45% $TiO_2/Fe_2O_3$ (1:1) | 10% cetyl alcohol |
| K | Zinc | 10% $TiO_2/Fe_2O_3$ (1:1) | 20% sodium thiosulphate |
| L | Glycerol | 40% $TiO_2/Fe_2O_3$ (1:1) | 20% cetyl alcohol |

Sodium thiosulphate was found to have low solubility in the zinc based creams but to have good thermal resistance by virtue of a high latent heat of fusion. A total of 14 trials were carried out. The first two trials had no cream applied to any of the heat dose gauges to act as a further control, confirming that the heat dose calculation would give the same result irrespective of the starting temperature of the gauge.

Figure 6:
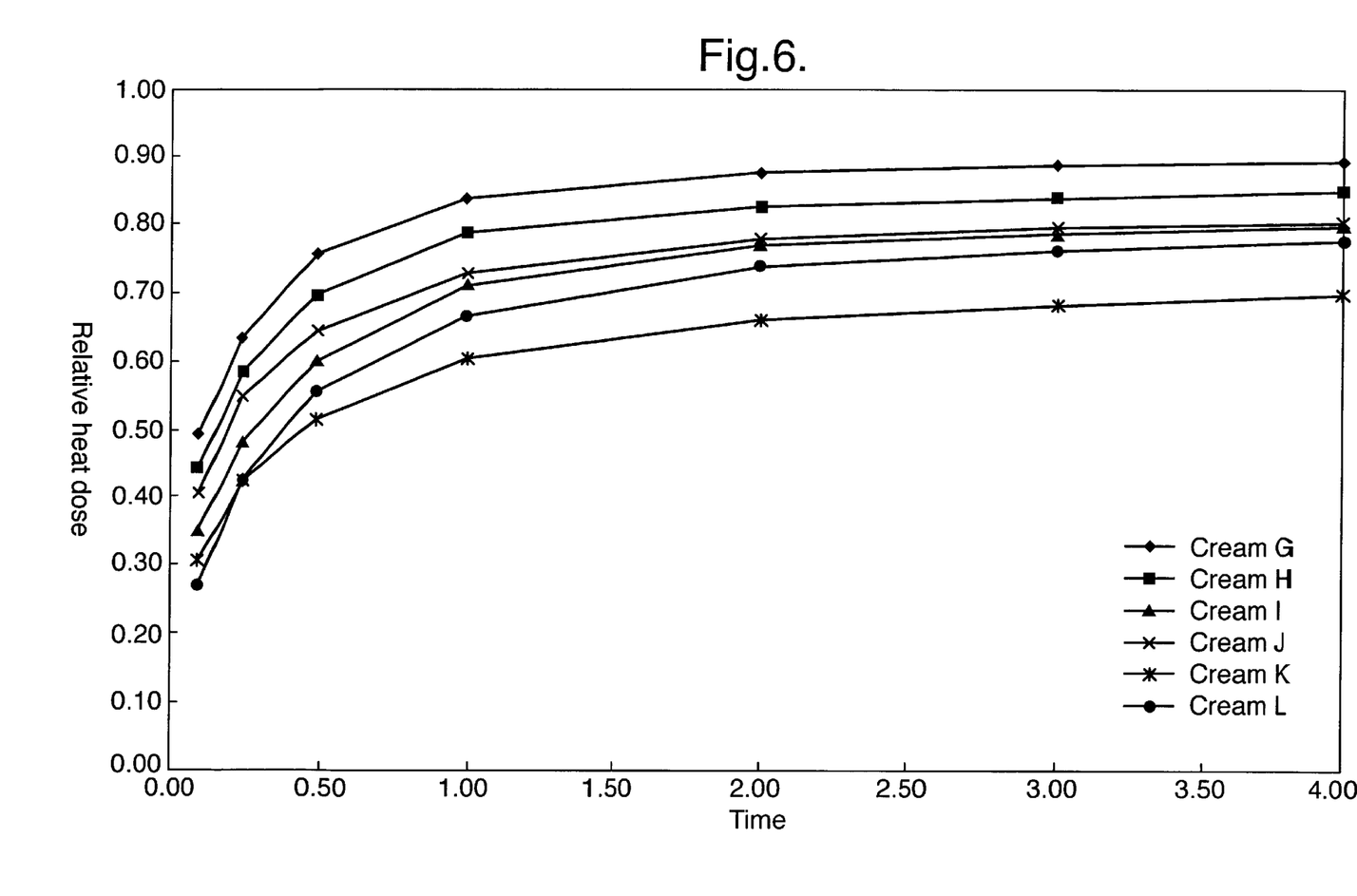
FIG. 6 is a graph showing the relative heat dose performance data for a number of examples G–L of the cream in accordance with the present invention as measured using the experimental arrangement shown in FIG. 5.

All six creams G to L were used in the trials. Individual cream types were rotated around the block of gauges as repeat trials were conducted. A total of twelve repeats were carried out with each cream type. The relative heat dose performance data for the six creams are shown in FIG. 6. The data shown are mean values and indicate that all of the creams are effective at reducing the heat dose experienced by the gauges. When considering the mean values only, cream K is more effective over all time intervals than any of the other creams. A comparison of the data for creams G, H and K indicates that the performance of these zinc based creams is enhanced by increasing the proportion of melt additive in the cream. These zinc based creams all comprise 10% w/w of the oxide mixture.

A comparison of the data for creams I, J and L shows that there is little difference in performance between these three creams with a glycerol base. Creams I, J and L contain 0%, 10% and 20% w/w melt additive respectively. L, the cream with the highest proportion of melt additive performs slightly, but not significantly, better than the other two creams. This indicates that, in this case, the concentration of melt additive has little effect on performance. However, creams I, J and L contain 50%, 45% and 40% w/w reflective additive and therefore any positive effect of the melt additive may be offset by a decrease in performance caused by a decrease in reflective additive content.

Figure 7:
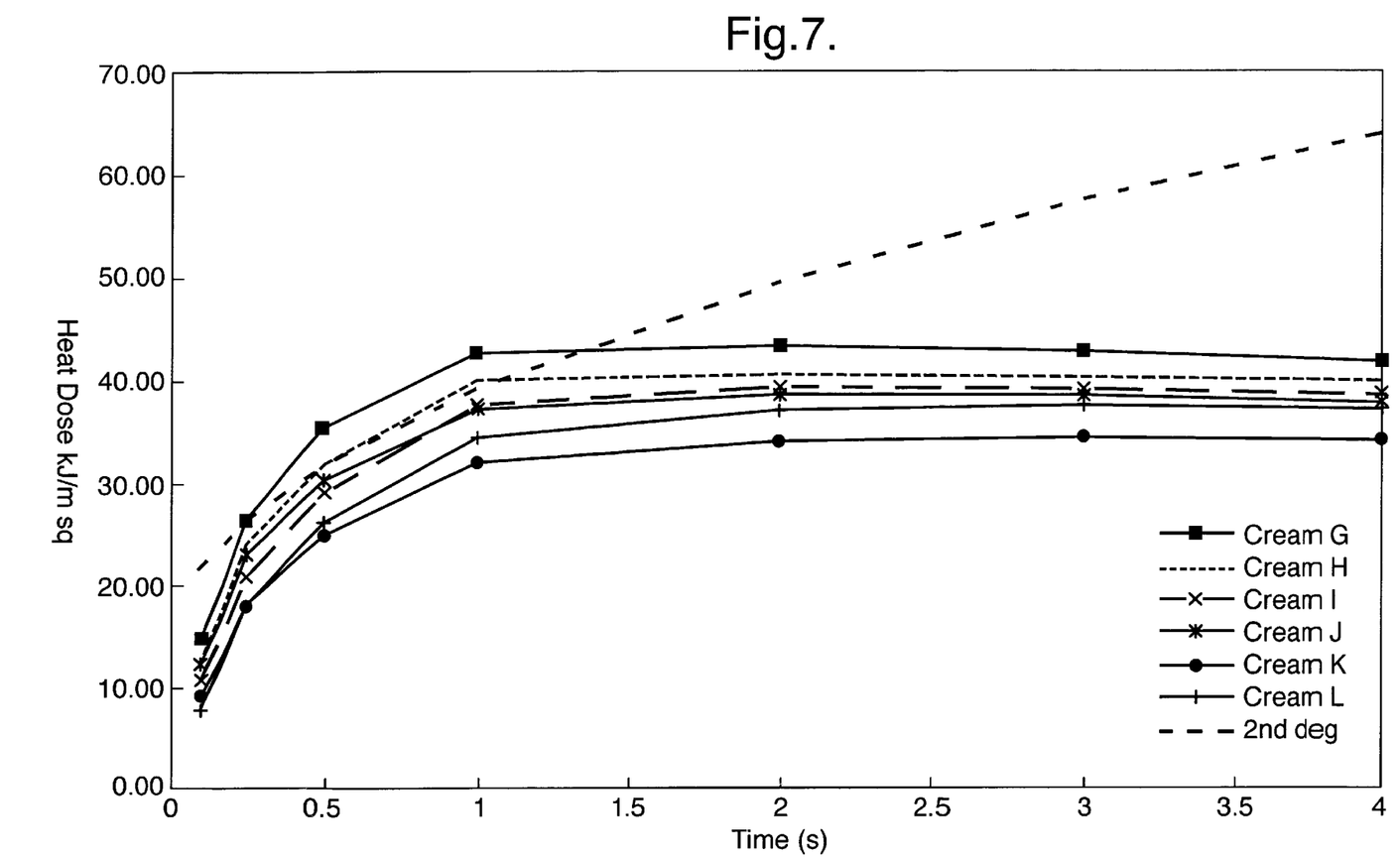
FIG. 7 is a graph showing heat dose performance data for creams G–L compared with data derived from a $2^{nd}$ degree burn model to give an indication of the potential risk of burn injury.

FIG. 7 shows the heat dose performance data for creams G–L as determined by the experimental layout of FIG. 5 in comparison with theoretically-derived data for the heat dose required to generate a $2^{nd}$ degree burn. The data for the creams are mean values calculated at given time periods after the initiation of the explosion. Of creams G–L, only G fails to protect the heat gauge from heat doses that would be large enough to generate $2^{nd}$ degree burns. One should note that G only appears to fail over a short time period.

EXAMPLE 3

In Vitro Assessment.

The effect of absorption of cream elements by the skin was investigated to determine the effect of absorption through the skin on the heat-reflecting and scavenging properties of the cream over an eight hour time period. To do this the temperature change beneath human epidermal membranes covered with candidate creams was measured when challenged at various timepoints after application. An epidermal membrane represents the outer dead layer of skin (stratum corneum) which forms the barrier to chemical penetration. Immediately beneath the stratum corneum is the living tissue first affected during burning and the temperature change here indicates the potential to cause a burn. Note that the absorption of cream constituents would have occurred in the experiments reported here just as it would on living tissue.

Experiments were carried out in a modified Franz type diffusion cell. These cells have a donor chamber and a receptor chamber separated by a semi-permeable membrane, which for the purposes of these experiments is human epidermal membrane. The receptor chamber is filled with a receptor fluid which may be sampled through a sampling arm without disturbing the membrane thus enabling estimation of a chemical diffusion from the donor chamber through the membrane. A surface area of 2.54 $cm^2$ was available for diffusion. In these experiments a support gauze which is normally used to prevent physical damage to the delicate membranes placed in the cells was modified by spot welding a thermocouple to its centre enabling changes in temperature just below the surface to be measured.

Tissue Preparation and Integrity

Human epidermal tissue obtained from elective reductive surgery patients and showing no signs of pathology was used in the experiments. After removal of subcutaneous fat deposits, the skin was placed in water at 60° C. for 45 seconds and the epidermal membranes were scraped away by blunt dissection. These membranes could be floated on water and mounted on aluminium foil for freezing and storage at −25° C. until required. Twenty four hours before the experiment epidermal membranes were thawed and cut into pieces sufficient to cover the receptor chamber of glass Franz type diffusion cells. Each receptor chamber of the cells was filled with 1:1 ethanol:water which was stirred throughout the experiment by a magnetic follower. Diffusion cells were mounted on a heated plate and flat bed stirrer (Whatman UK) and were maintained at 30 ±1° C. until challenged with heat. The structural integrity of the membranes was then tested by measuring the penetration of tritiated water. 1 $\mu$Ci of tritiated water was applied to the upper surface of the membranes in 1 mL and after 20 minutes 20 $\mu$L samples of receptor fluid were added to 5 mL of scintillant and the radioactivity in the samples estimated in a Rack Beta scintillation counter. Any membrane which permitted the penetration of more than 10% of the applied dose during 20 minutes was regarded as damaged during preparation and rejected from the study.

Application of Candidate Creams

At the beginning of the experiment 0.1 mL of candidate thermal barrier cream was applied to the surface of the epidermal membrane from a 1.0 mL disposable syringe and spread evenly over the surface with the plunger of the syringe. The mass of the cream applied was recorded as the difference between the mass of the syringe before and after application. From the mass of the cream applied a nominal thickness of cream was calculated assuming unit density.

Challenge of Creams with Heat

Cells were removed from the heated stirring plates and mounted on a plate which could be moved under a heater (3 kW running at 770±10°C.). Changes in temperature immediately beneath the epidermal membranes were measured by a thermocouple spot welded to the support gauze and connected to a Nicolet Multipro digital oscilloscope. Concurrently a reference thermocouple was placed under the heat source. A summary of the analysis of this data is given below. Note that the heat source gave a continuous steady flux, unlike the transient flux of a detonation.

Study Design

Two candidate creams, L and K, were tested. The study was carried out in three separate experiments. The first two experiments tested each cream individually at various time intervals after application and the final experiment controlled for inter-experiment variation by testing both creams concurrently at 4 hours after application. Each cream was tested on skin from between 2 and 6 individuals (Table 5) at 1 minute, 2, 4 & 8 hours after application.

Calculations

In order to calculate heat flux in the diffusion cells, a value of 3200 J/kg.K for the heat capacity of the receptor fluid and a thermal conductivity of 0.6 W/m.K were assumed. Data are presented as mean values and SEM of total temperature change over 10 seconds of heating and of the relative heat flux over the same ten second period. Relative heat flux was calculated using the equation:

$$\text{Relative flux} = \frac{\text{Heat flux at sample thermocouple}}{\text{Heat flux at reference thermocouple}} \qquad \text{Equation 1}$$

TABLE 5 details of cream layers applied for in vitro experiments

| Cream | Time of challenge | Weight of applied cream (mg) | N | Thickness of applied cream (mm) | Number of donors |
|---|---|---|---|---|---|
| L | 1 Min | 86.2 ± 5.6 | 6 | 0.339 ± 0.02 | 6 |
| L | 1 Hour | 77.6 ± 4.2 | 6 | 0.306 ± 0.02 | 6 |
| L | 2 Hours | 85.9 ± 5.1 | 6 | 0.338 ± 0.02 | 5 |
| L | 4 Hours | 80.6 ± 1.7 | 6 | 0.317 ± 0.01 | 6 |
| L | 8 Hours | 81.9 ± 3.8 | 6 | 0.323 ± 0.01 | 5 |
|   | Blank | 0 | 5 | 0 | 3 |
| All cells treated with L |   | 82.4 ± 1.8 |   | 0.325 ± 0.01 |   |
| K | 1 Min | 70 ± 5.9 | 4 | 0.275 ± 0.02 | 4 |
| K | 1 Hour | 69.3 ± 5.6 | 3 | 0.273 ± 0.02 | 3 |
| K | 2 Hours | 64.2 ± 15 | 3 | 0.253 ± 0.06 | 2 |
| K | 4 Hours | 74.1 ± 2.4 | 4 | 0.292 ± 0.01 | 4 |
| K | 8 Hours | 69.1 ± 5.8 | 4 | 0.272 ± 0.02 | 2 |
|   | Blank | 0 | 4 | 0 | 4 |

TABLE 5-continued details of cream layers applied for in vitro experiments

| Cream | Time of challenge | Weight of applied cream (mg) | N | Thickness of applied cream (mm) | Number of donors |
|---|---|---|---|---|---|
| All cells treated with K | | 69.6 ± 2.9 | | 0.274 ± 0.01 | |
| L | 4 Hours | 82.9 ± 4.3 | 6 | 0.326 ± 0.03 | 3 |
| K | 4 Hours | 73.3 ± 6.4 | 6 | 0.288 ± 0.03 | 3 |
| | Blank | 0 | 8 | 0 | 3 |

N is the number of diffusion cells taken from the number of donors indicated.
Data are mean ± SEM of the number of diffusion cells, and thickness assumes unit density (i.e. 1 g/mL).

Results

Application and spreading of creams using a disposable syringe plunger produced a layer which completely covered the exposed epidermal membrane. There were small sample-to-sample variations in the weights of layers of a particular cream and hence the nominal thickness of the layer (table 5). A larger difference existed between the mean mass of the layer of each of the two creams, with an overall average of 69.6 (±2.9) mg of cream K being applied, compared to a mean 82.4 (±1.8) mg of cream L. The nominal thicknesses calculated from these weights (assuming unit density; table 5), was 0.325±0.01 mm for cream L and 0.274±0.01 mm for cream K. This should be interpreted with the knowledge that the creams contained particulate material so the layers could not be uniform.

The total change in temperature at the thermocouple was similar under membranes challenged after all periods of application and similar to those of the reference thermocouple.

There was a larger increase in temperature when no cream was applied. The heat flux at the reference thermocouple was constant for the duration of its exposure to heat (data not shown).

The relative heat flux through both creams increased rapidly over the first second of exposure and then more slowly between 1 and 8 seconds of exposure. After 8 seconds the heat flux was erratic due to movement of the cells as it was withdrawn from beneath the heat source. At all points during exposure to heat, the membranes without cream experienced a higher flux than any of the membranes treated with cream. There was little difference between the flux across creams which had been on the epidermal membranes for 1, 2, 4 or 8 hours. The reduction in heat flux compared to skin not treated with cream was greater during the first second of heating (80–90% for both creams). During this 1 second period, the cream applied only one minute prior to the exposure to heat provided better protection than cream which had been applied 1, 2, 4 or 8 hours previously. After the first second of heating the reduction in heat flux compared to untreated skin was similar for both creams (10–30%). Furthermore, the reduction in heat flux after the initial 1 second period did not vary significantly with the period for which the cream had been applied to the skin. There was no difference in the flux across membranes treated with creams K or L and exposed after having been left for 4 hours concurrently.

Figure 8:
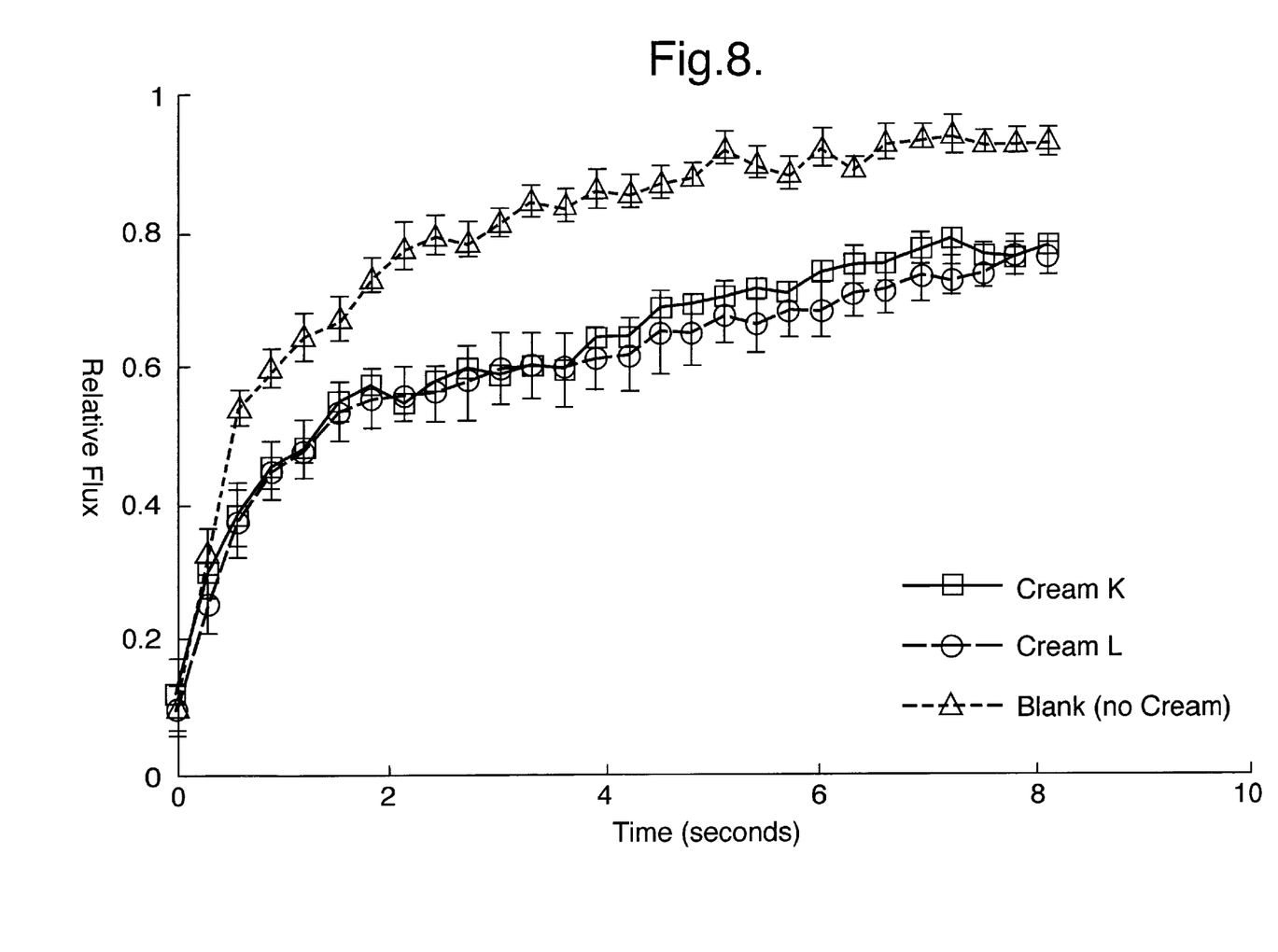
FIG. 8 shows the relative heat flux performance data over an 8 second exposure for creams K and L.

FIG. 8 shows the relative heat flux over an 8 second exposure for creams L and K and the bare gauge. Both creams had been applied for 4 hours. This illustrates that both creams provide a reduction in heat flux across the skin throughout the 8 second period. Furthermore, this figure illustrates that both creams provide similar protection.

Creams according to the present invention are effective in reducing heat flux through the skin for approximately 8 hours after application and hence are effective in the prevention of burns.

What is claimed is:

1. A barrier cream for the mitigation of burns, the cream comprising an oil-based base cream, 40–50% w/w of a 1:1 w/w mixture of titanium dioxide and ferric oxide and from 0 to 20% w/w of a melt additive.

2. A barrier cream according to claim 1 wherein the melt additive has a latent heat of fusion of at least 50 $Jg^{-1}$.

3. A barrier cream according to claim 1 wherein the melt additive has a melting point below 55° C.

4. A barrier cream according to claim 1 wherein the melt additive comprises an alkali metal salt, alcohol fat or wax.

5. A barrier cream according to claim 1 wherein the melt additive comprises a fatty acid or derivative.

6. A barrier cream according to claim 1 wherein the melt additive is selected from the group consisting of methyl 4-(hydroxymethyl)benzoate, 4-phenylbutyric acid, 1,4-benzodioxan-6-carboxaldehyde, methyl 4-methoxybenzoate, 4-methylbenzhydrol and methyl 7-oxooctadecanoate, cetyl alcohol and sodium thiosulphate.

7. A barrier cream according to claim 6 wherein the melt additive is methyl 7-oxooctadecanoate or cetyl alcohol.

8. A barrier cream according to claim 1 wherein the barrier cream is colored.

* * * * *